United States Patent [19]
Galando et al.

[11] Patent Number: 6,131,690
[45] Date of Patent: Oct. 17, 2000

[54] MOTORIZED SUPPORT FOR IMAGING MEANS

[76] Inventors: John Galando, 17007 NE. 130$^{th}$ St., Redmond, Wash. 98052; John K. Grady, 43 Slough Rd., Harvard, Mass. 01451; Joseph Giamona, 2523 - 291$^{st}$ Ave., Carnation, Wash. 98014

[21] Appl. No.: 09/087,393

[22] Filed: May 29, 1998

[51] Int. Cl.$^7$ .............................. B62D 1/00; H05G 1/02
[52] U.S. Cl. ..................... 180/411; 180/19.1; 378/198
[58] Field of Search ................... 378/193, 197, 378/198; 280/79.11, 47.43, 62, 64; 180/19.1, 19.3, 411, 412

[56] References Cited

U.S. PATENT DOCUMENTS

| | | |
|---|---|---|
| 2,232,014 | 2/1941 | Simon . |
| 2,818,510 | 12/1957 | Verse . |
| 3,037,784 | 6/1962 | Williams ............................. 280/11.26 |
| 3,081,106 | 3/1963 | Budd ................................... 280/11.26 |
| 3,143,749 | 8/1964 | Buchholz et al. .................... 280/43.2 |
| 3,463,506 | 8/1969 | Drake . |
| 3,696,881 | 10/1972 | Gordon . |
| 3,879,053 | 4/1975 | Chvala . |
| 4,257,619 | 3/1981 | Fisher . |
| 4,481,656 | 11/1984 | Janssen et al. ........................ 378/196 |
| 4,697,661 | 10/1987 | Pajerski et al. ......................... 180/6.5 |
| 4,716,581 | 12/1987 | Barud .................................... 378/198 |
| 4,866,751 | 9/1989 | Louiday ................................ 378/196 |
| 4,868,845 | 9/1989 | Koropp ................................. 378/204 |
| 4,872,192 | 10/1989 | Hahn et al. ............................ 378/181 |
| 4,887,287 | 12/1989 | Cobben .................................. 378/198 |
| 4,912,754 | 3/1990 | Van Steenburg ...................... 378/209 |
| 4,955,046 | 9/1990 | Siczek et al. .......................... 378/197 |
| 4,960,271 | 10/1990 | Sebring ................................. 269/323 |
| 4,964,152 | 10/1990 | Kaul et al. ............................. 378/198 |
| 5,008,921 | 4/1991 | Kaul et al. ............................. 378/198 |
| 5,048,071 | 9/1991 | Van Steenburg ...................... 378/209 |
| 5,147,002 | 9/1992 | Hughes .................................... 180/6.5 |
| 5,156,166 | 10/1992 | Sebring ................................. 128/845 |
| 5,283,823 | 2/1994 | Morris .................................... 378/198 |
| 5,325,935 | 7/1994 | Hirooka et al. . |
| 5,350,033 | 9/1994 | Kraft ...................................... 180/167 |
| 5,386,453 | 1/1995 | Harrawood et al. .................. 378/196 |
| 5,425,068 | 6/1995 | Schaefer et al. ....................... 378/197 |
| 5,425,069 | 6/1995 | Pellegrino et al. .................... 378/198 |
| 5,426,683 | 6/1995 | O'Farrell, Jr. et al. ................ 378/197 |
| 5,475,730 | 12/1995 | Galando ................................ 378/157 |
| 5,499,284 | 3/1996 | Pellegrino et al. .................... 378/198 |
| 5,503,416 | 4/1996 | Aoki et al. ........................... 280/79.11 |
| 5,544,217 | 8/1996 | Kadowaki et al. ................... 378/198 |
| 5,583,909 | 12/1996 | Hanover ................................ 378/197 |
| 5,586,162 | 12/1996 | Grichnik ............................... 378/198 |
| 5,702,117 | 12/1997 | Geelhoed . |
| 5,835,557 | 11/1998 | Malmstrom ........................... 378/197 |
| 5,901,200 | 5/1999 | Krause .................................. 378/198 |

FOREIGN PATENT DOCUMENTS 3-251230  11/1991  Japan .............................. A61B 6/00

OTHER PUBLICATIONS

Phillips brochure titled "BV212, Broaden your vision" (date of publication unknown).

*Primary Examiner*—Lanna Mai
*Assistant Examiner*—Ruth Ilan

[57] ABSTRACT

A mobile motorized base, cart, or carriage apparatus for moving medical imaging equipment about a portion of a body of a patient. The apparatus includes a lower chassis and an upper chassis. The upper chassis can be moved in a selective and controlled manner between a retracted and extended position. The lower chassis has precision movement to mechanically guide and advance the medical imaging equipment about the patient. The movement is enabled by the use of separate drive motors and rotator motors for the drive wheels. An omni-directional third wheel is used to support the upper chassis relative to the floor.

22 Claims, 8 Drawing Sheets

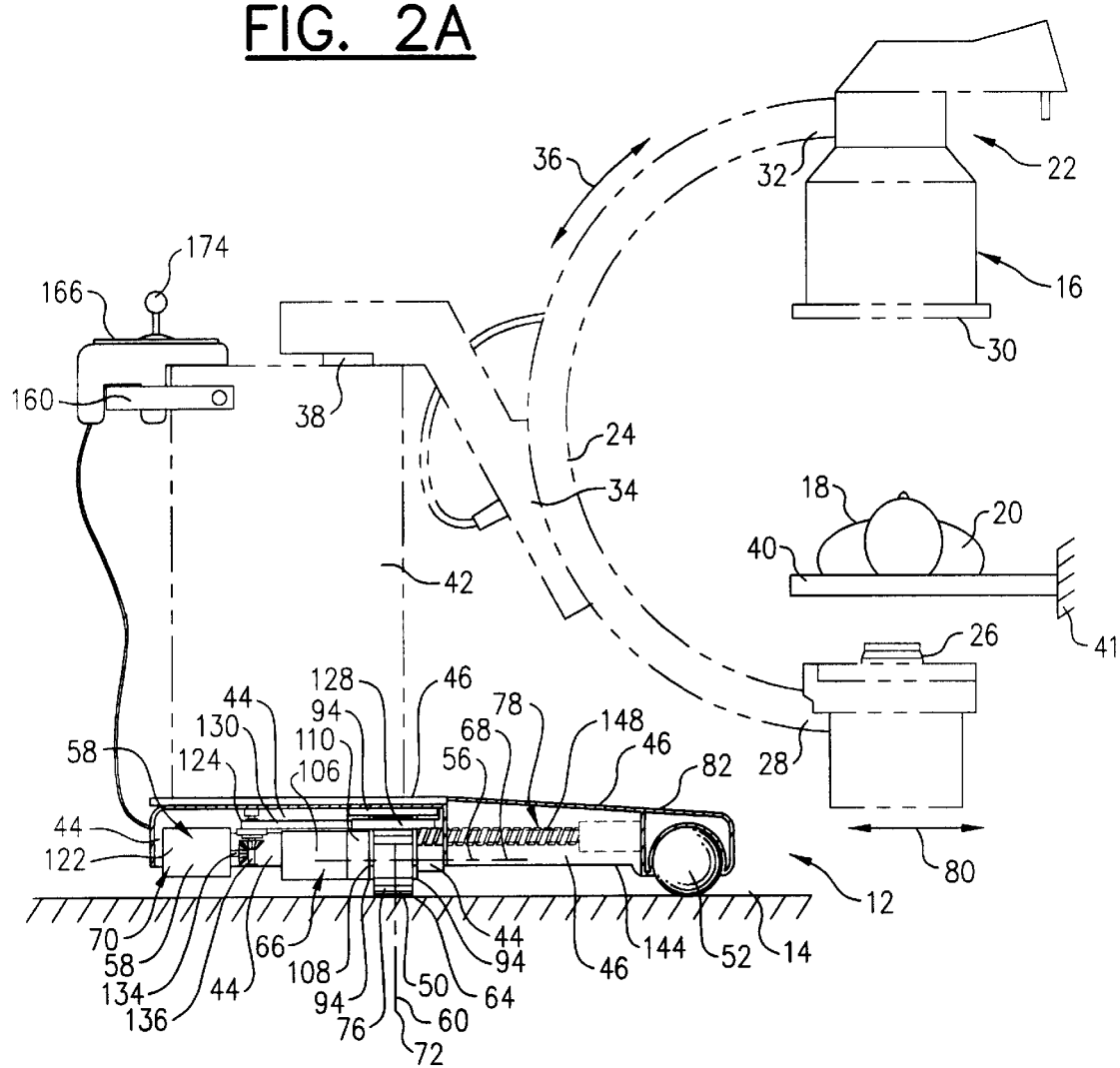

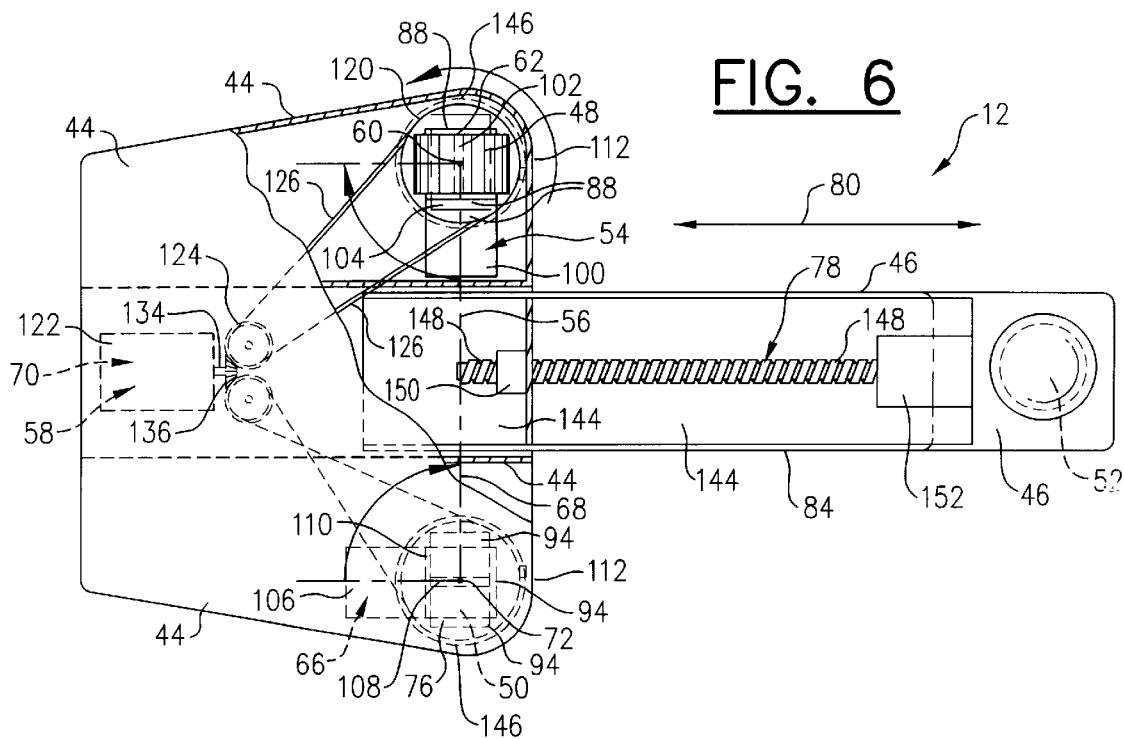
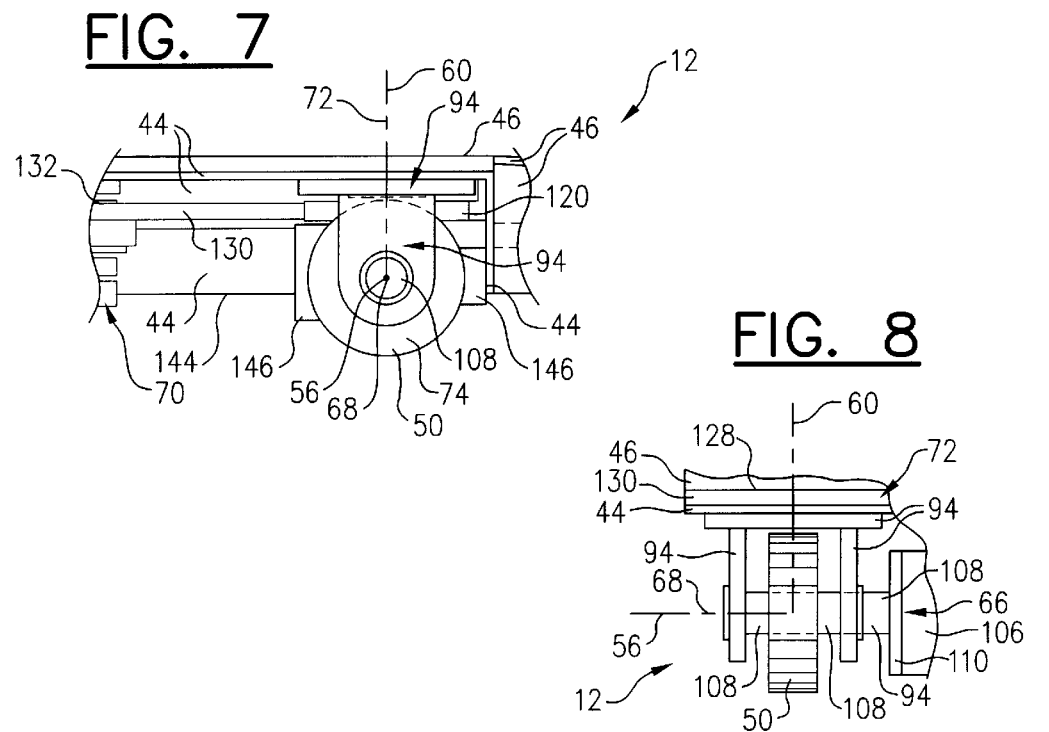

MOTORIZED SUPPORT FOR IMAGING MEANS

TECHNICAL FIELD

This invention relates to motorized supports for medical imaging systems and methods of manufacture and use thereof, and, more particularly, to mobile imaging apparatus having precision propulsion means to mechanically guide, advance and retract medical imaging means about a body of a patient.

BACKGROUND ART

There are certain medical procedures, such as interventional or endovascular procedures wherein imaging of the blood vessels and imaging of devices within the blood vessels, that are typically conducted using C-arm imaging apparatus.

Once the patient is properly situated on a table top, the C-arm of such systems is caused to pass or sweep around the patient.

Certain systems are affixed to the ceiling and/or floor. Such systems require an extensive support structure. One of the disadvantages to these systems is that since they are fixed to the building, they require a dedicated room. Fixed attachment within a dedicated room limits the types of procedures that can be done with such equipment and creates scheduling problems.

Other disadvantages are that since the equipment is fixed to the building and require support structures, the dedicated room must be extensively prepared. There are expensive construction costs. Time required to construct, modify and/ or prepare the dedicated room and install the associated systems is costly, creates problems within what is supposed to be a sterile environment. This is particularly true if such systems are installed in or near operating rooms. Furthermore, such rooms cannot be used during the construction, modification, preparation, and installation phases associated with such equipment and systems.

Ceiling suspended systems can create additional problems within what must be a sterile environment within operating rooms. For example, debris must not fall from overhead structures and equipment or from their related and required support structures, that are often positioned directly above the patient and operating table. Furthermore, suspended systems can cause interference with other overhead equipment and devices, such as lighting, sterile room ventilation equipment, and anesthesia devices, that are often found within operating rooms.

Due to excessive costs, immobility, and the inflexibility of using such equipment within dedicated rooms, mobile or portable C-arm x-ray imaging systems were created. One example is the Philips BV212 x-ray system. Such systems were sufficiently smaller and mobile to enable the device to be pushed or pulled manually into a surgery or operating room. In other words, such devices were manually pushed or pulled around from room to room within a hospital or clinic.

Once such C-arm is placed into position along the patient table, the imaging procedures of the blood vessels or tracking/chasing of devices within the blood vessels were performed. During these procedures, the C-arm device was manually pushed or pulled along the length of the patient table. In most cases, multiple positioning is required in order to perform the entire procedure. For example, typically, a single image is taken with the C-arm over the chest portion of the patient. When the time arrives, a second image is taken with the C-arm repositioned over the thighs of the patient. Thereafter, the C-arm is again repositioned down to the patient's lower extremities where another imaging process is performed. Because of the size, weight, and multitude of simultaneous functions needed to performed with the mobile C-arm device, it is very difficult and burdensome to accomplish accurate movement of such systems.

In addition, because such mobile C-arm systems are manually maneuvered, it is arduous, if not impossible, to simultaneously move the device longitudinally and vertically at the same time, such as within an X-Y coordinate system.

Furthermore, the tracking of medical devices inserted into blood vessels requires rapid movement of the mobile C-arm device in a back and forth series. For example, the chasing or tracking of a catheter tip as it enters a knee area and then is brought back and forth up into the thigh area of a patient, requires precise, quick movements which are extremely difficult to perform by manual maneuvering of the C-arm device. This task is very cumbersome, difficult, and often impossible to accomplish.

In summary, heretofore C-arm imaging or imaging equipment were either permanently fixed and secured to the floor and/or ceiling of a dedicated room, or consisted of mobile C-arm imaging systems that were manually pushed or pulled throughout the hospital. The key words here are "apermanently", "fixed" and "manually." In particular, mobile C-arm imaging systems did not have motorized carts or carriages.

There were some radiographic units, used to take a plain X-ray of a patient's body, that were attached to a minimally motorized base, cart, or carriage. However, such bases, carts, or carriages were motorized only to move in a limited fashion to transport such equipment down a hallway. The motorized bases, carts, or carriages on these radiographic systems were used just to get the unit from the radiology department up to the patient's beds, because of the size and weight of the equipment.

Such radiographic equipment is extremely heavy, bulky, and most workers within a hospital or clinic are generally incapable of pushing such heavily weighted units. For example, some of these minimally mobile radiographic units weigh about three-hundred to eight-hundred pounds (300 to 800 lbs.) each. Consequently, they are provided with large, imprecise, motorized wheels that simply drive the unit into an elevator or down a hallway. Such motorized wheels are not used during the performance of the medical procedures.

As may be appreciated, the manipulation of such heavy, massive, and bulky equipment requires a considerable amount of space and is thus of limited utility where access is limited. The space requirement for operation of this equipment also necessitates use within a considerably larger room. Not only does the manipulation of this equipment require additional space, but the cumbersome size and shape of the equipment itself severely limits the utility of these devices.

Once positioned adjacent to a patient, such equipment must be manhandled into position and the wheels are locked into a stationary, nonmoving position. Due to their excessive weight, these devices are quite difficult to push.

Once such equipment is placed into position, the equipment stays put, fixed, and is not moved until the procedure is completed. In other words, such equipment is not motorized when placed adjacent to a patient.

The following patents and materials describe a wide variety of different imaging machinery: Janssen et al. (U.S.

Pat. No. 4,481,656, issued Nov. 6, 1984); Pajerski et al. (U.S. Pat. No. 4,697,661, issued Oct. 6, 1987); Barud (U.S. Pat. No. 4,716,581, issued Dec. 29, 1987); Louiday (U.S. Pat. No. 4,866,751, issued Sep. 12, 1989); Koropp (U.S. Pat. No. 4,868,845, issued Sep. 19, 1989); Hahn et al. (U.S. Pat. No. 4,872,192, issued Oct. 3, 1989); Van Steenburg (U.S. Pat. No. 4,912,754, issued Mar. 27, 1990); Sebring (U.S. Pat. No. 4,960,271, issued Oct. 2, 1990); Kaul et al. (U.S. Pat. No. 5,008,921, issued Apr. 16, 1991); Van Steenburg (U.S. Pat. No. 5,048,071, issued Sep. 10, 1991); Hughes (U.S. Pat. No. 5,147,002, issued Sep. 15, 1992); Sebring (U.S. Pat. No. 5,156,166, issued Oct. 20, 1992); Kraft (U.S. Pat. No. 5,350,033, issued Sep. 27, 1994); Harrawood et al. (U.S. Pat. No. 5,386,453, issued Jan. 31, 1995); Schaefer et al. (U.S. Pat. No. 5,425,068, issued Jun. 13, 1995); Pellegrino et al. (U.S. Pat. No. 5,425,069, issued Jun. 13, 1995); O'Farrell, Jr. et al. (U.S. Pat. No. 5,426,683, issued Jun. 20, 1995); Galando (U.S. Pat. No. 5,475,730, issued Dec. 12, 1995); Pellegrino et al. (U.S. Pat. No. 5,499,284, issued Mar. 12, 1996); Aoki et al. (U.S. Pat. No. 5,503,416, issued Apr. 2, 1996); Kadowaki et al. (U.S. Pat. No. 5,544,217, issued Aug. 6, 1996); Hanover (U.S. Pat. No. 5,583,909, issued Dec. 10, 1996); Tanaka (Japan Patent No. 3-251,230(A), issued Nov. 8, 1991); and Philips brochure titled "BV212, Broaden your vision" (date of publication unknown).

The primary problems with the aforementioned systems include the requirements and limitations that: (a) a specially constructed or renovated and extremely expensive room be built to house such equipment; (b) such room must be dedicated solely to use with such equipment; (c) such equipment is inappropriate for use within a sterile environment of an operating room; (d) a patient be transported to the equipment; (e) such heavy and bulky mobile equipment be manually pushed or pulled through a crowded hallway or corridor; (f) such heavy and bulky minimally mobile equipment be manually pushed, manipulated, positioned, repositioned, and then removed from a traditionally very small operating room; (g) use of such heretofore known devices is extremely time consuming because the device must be manually moved and repeatedly repositioned; (h) use of such devices sometimes result in excessive exposure to x-rays along a patient's body and excessive contrast agents being injected into the patient's body; and/or (I) such mobile systems cannot perform multiple tasks simultaneously.

The results of these drawbacks and limitations have far reaching effects in terms of: (a) increasing the cost to construct and maintain special facilities to house such equipment; (b) jeopardizing the safety of patients by prolonging the procedure, exposing the patient to additional x-rays, and increasing the amount of contrast agents; (c) creating a difficult environment within which these medical procedures are conducted due to the manually pushing and pulling of heavy and bulky equipment; (d) requiring the attention of specially skilled individuals to manhandle and operate such equipment; and (e) obtaining less than optimal results from the crude, inaccurate, and inexact methods currently used to position such equipment, all of which significantly increase the cost to perform these medical procedures.

It is firmly believed that the above-listed patents and information, whether taken alone or in combination, neither anticipate nor render obvious the current invention. The foregoing explanation does not constitute an admission that such disclosures or information are relevant or material to the appended Claims. Rather, such disclosures and information relate only to the general field of the current invention and constitute the closest art of which the inventor is aware.

DISCLOSURE OF INVENTION

The current invention overcomes all of the above-identified disadvantages and provides numerous advantages heretofore unavailable within the medical profession.

Heretofore, most scanning and imaging equipment was required to be permanently placed within a special room. This invention now permits such equipment to be used in a mobile manner and is not fixed to the ceiling or floor.

Most notably, this invention provides doctors, surgeons and medical technicians with a mobile scanning and/or imaging apparatus that can be wheeled into a room of relatively confined space to conduct a progressive and continual scan of a patient's body, without having to move the patient or manually reposition the apparatus during the procedure. For example, this invention can be used with a mobile C-arm x-ray imaging system for conducting a continuous imaging of blood vessels from the aorta and progressively sweep down the patient's body, and/or to track devices within blood vessels in an automated and more detailed and specialized manner. This invention allows the procedures to be performed in a faster, easier, and more efficient and effacaious manner with less complications to both the operator and to the patient. Furthermore, use of this invention is safer for the patient that the devices heretofore known in the art.

In other words, the apparatus of this invention provides an easily actuated, self-propelled, precision propulsion means for mechanically guiding, advancing, and retracting medical scanning and/or imaging means about the body of the patient. The apparatus may be actuated via a remote control device, a radio control device, a body mounted control device, or any other desired device and/or placement.

The current invention includes an apparatus that basically defines a motorized cart, carriage or support base upon which a piece of mobile medical scanning and/or imaging equipment is operatively attached, secured, transported, and operated. The apparatus has a plurality of wheels that can be either totally motorized or switch back and forth between being motorized and manually manipulated.

Within the preferred embodiment of this invention the apparatus has a first drive wheel and a second drive wheel which are, respectively, operatively attached to an electrically powered first drive motor and a second drive motor.

Any drive motor or other motor used within this invention could comprise a linear motor or servo-drive motor with or without its associated electronic gearing and electronic line shafting. The linear motor or servo-drive motor is operatively secured to the frame, and, more particularly, to either an upper chassis or to a lower chassis thereof.

Preferably, the first drive wheel and the second drive wheel are secured to the apparatus in such a manner that they have a co-linear or parallel orientation one to another.

Alternatively, the first drive wheel and the second drive wheel may be operatively connected to their respective drive motors via use of a single or plurality of ninety degree gear drives.

Within the preferred embodiment of this invention, the first drive wheel and the second drive wheel generally comprise heavy-duty industrial casters that are driven by twin electric drive motors with encoders and rotate on thrust bearings.

The electronic coupling and/or activation of the independent first drive wheel and the second drive wheel can be used to control the relative rotation of one drive wheel to the other drive wheel, depending upon the direction and rate of rotation. When the operator directs the apparatus to traverse in a straight line, the drive wheels are coupled together at a direct one to one (1:1) ratio, as they would be in a mechanical drive shaft coupled system.

When a direction is given to turn, the relative ratios can be electronically controlled to allow one drive wheel to essentially pivot around, outrun, or fall-behind the rotation of the other drive wheel while both drive wheels remain rotating. This ratio-metric control functionality of the first drive wheel and the second drive wheel enable the operator to steer the apparatus and align the apparatus and accompanying imaging means to the longitudinal axis of the examination table.

Alternatively, one or both of the drive wheels can be decoupled to a non-driven position.

The apparatus also has an omnidirectional third wheel that is captured within an ultra high molecular weight polyethylene (UHMW). This non-driven front or third wheel is mounted to the apparatus using a swivel caster type of a base which allows the third wheel to conform to nearly any desired direction of travel.

Within an alternative embodiment of this invention, the third wheel may be provided with means for actively steering the apparatus, rather than mounting the third wheel to a passive caster type of swivel base.

It is very important to note that within this invention the apparatus is moved relative to an underlying floor. It is believed that this feature is in stark contrast to the devices heretofore known within the art, which are either permanently attached or secured to the floor or to a ceiling, or are wheeled around manually and the wheels are not motorized. Furthermore, the powered drive wheels of this invention are an integral feature in the performance of the medical scanning and/or imaging procedure. In other words, the powered drive wheels of this invention are progressively activated and used during and/or throughout the scanning and/or imaging procedure.

In addition to attaching powered motors on the underlying first drive wheel and the second drive wheel, the apparatus of this invention uses two distinct and separate chassises or carriages, namely, a lower chassis and an upper chassis. The first drive wheel and the second drive wheel are operatively secured to the lower chassis. The omnidirectional third wheel is operatively secured to the upper chassis.

Although the third wheel could simply be a regularly gimbled wheel, within the preferred embodiment of this invention, the third wheel comprises a spherical ball which is placed within a specially designed receptacle positioned within the upper chassis.

The upper chassis is placed upon and operatively secured to the lower chassis in such a manner that they act and operate in unison. However, the upper chassis can be moved from a retracted position to an extended position relative to the lower chassis. In other words, the length of the apparatus can be expanded or contracted in an overlapping or telescopic manner by having the upper chassis move away from or toward a superimposed position above the lower chassis.

A portion of the upper chassis extends outwardly from the lower chassis. It is upon this extended portion of the upper chassis that the omnidirectional third wheel is operatively secured. Thus positioned, the first drive wheel, the second drive wheel, and the omnidirectional third wheel form a three-point or tripod support for the scanning and/or imaging equipment.

The balanced structure of this apparatus and the narrow leading leg of the upper chassis, which contains and houses the third wheel, provides a wide opening to offer a relatively open work space that permits the doctor or technician to be close to the patient. The structure of this invention also allows nearly unrestricted access and effortless movement into any imaging position about the patient.

It is important to note that the scanning and/or imaging equipment is at least partially supported and secured to the upper chassis. Consequently, when the upper chassis is moved to an extended position, the overlying scanning and/or imaging equipment is similarly moved in the same direction. Since the third wheel and the extended portion of the upper chassis are also being moved at the same time, the center of gravity of the apparatus and of the scanning and/or imaging equipment remains safely between the third wheel, the first drive wheel, and the second drive wheel.

In other words, as the C-arm is extended towards a patient, the leading third wheel or spherical ball also moves toward the patient. Consequently, the center of gravity of the apparatus is always positioned behind the third wheel or spherical ball retained within the upper chassis. There is no danger that the apparatus would tip over onto a patient.

Within the preferred embodiment of this invention, the apparatus includes an electric drive unit which is secured between the upper chassis and the lower chassis. When activated, the electric drive unit rotates a worm screw or lead screw that is supported within a bearing and ball nut which is fixed to the frame or to one of the chassises. Rotation of the worm screw forces the upper chassis and the overlying C-arm scanner towards the patient or away from the patient, depending the direction of rotation of the worm screw. The electric drive unit may simply comprise a linear motor and associated reduction and/or connection gears.

There are different ways of securing the worm screw and associate machinery to the apparatus. For example, the drive unit can be positioned near to the third wheel. Alternatively, the drive unit can be positioned at or near the back or rear of the apparatus. Further alternatively, the drive unit could be positioned near or adjacent to a midsection or mid-distance between the third wheel and the rear or back of the apparatus. Of course, the drive unit could just as easily be placed at any other position along the length of the worm screw. Even though the position of the electric drive unit may be different in the various embodiments of this invention, the concepts taught herein are generally the same.

Alternatively, a rack and pinion system could be used instead of a worm screw. In other words, movement of the upper chassis either toward or away from the lower chassis and the patient may be accomplished and controlled by using a rack and pinion system and related, powered drive motor. For example, a double shafted motor may be operatively secured to the frame and to a pair of pinions, each of which engage a corresponding gear rack mounted to and/or placed within or adjacent to a V-track. Alternatively, one or more ball rails could be used. In essence, the relative movement of the upper chassis relative the lower chassis defines an indexing table.

The motorized first drive wheel, the second drive wheel, and the means for moving the upper carriage relative to the lower carriage are preferably controlled by using a keyboard, joystick, switch pad, pendant, body mounted control device, remotely controlled device, radio controlled device, voice activated device, and/or infrared control device.

The apparatus may also be provided with programmable hardware and/or software that will shorten the time to train operators to use the apparatus and/or reduce procedure time.

Within the preferred embodiment of this invention, a cabinet is mounted to the upper chassis. Within one embodiment of this invention, the control device comprises a control panel that is permanently secured to the cabinet that is operatively secured to the upper chassis. Alternatively, the control panel may comprise a hand-held device. Preferably, the control panel will include a joystick that enables the operator to move the scanning or imaging equipment forward, backward, to the left side, to the right side, up and down, and/or to tilt or rotate it along the C-arm path. There is also an on/off switch for the apparatus.

The control panel or mechanism can be connected to the housing with a cord or be radio controlled so that the operator can walk down the hall, sit on the other side of the room or behind a wall during operation of the apparatus. This permits remote activation of the scanner to protect the operator from excessive x-ray radiation. Furthermore, the scanning equipment can be brought via remote control into an operating room with the C-arm covered with sterile drapes, without touching the C-arm, and then can be moved or driven out once the procedure is completed.

The control panel may also comprise an optical or radio controlled lift-out unit with a receiving receptacle positioned or molded into the housing of the cabinet. If remote control is required or desired, the control panel could be lifted out of its receptacle.

Preferably, the cabinet is also provided with at least one handle or railing that can be used to steer and push or pull the device down a corridor or hallway when the first drive wheel and the second drive wheel are disengaged or decoupled from their respective drive motors. In essence, the handle enables the apparatus to be pushed down the hallway and when the apparatus is placed in a position a button can be pushed to make the drive wheels rotate and engage for operation of the procedure.

The handle can be used to steer, drive or manually push the apparatus when it is being transported down a hallway.

Handle grips may be positioned with the controls.

The control panel may also be placed within the handle or railing of the cabinet, with the control buttons being placed o n the inside of the handle or railing.

If a mobile C-arm x-ray device is used with this invention, additional mobility will be provided. For example, a mobile C-arm x-ray device typically has a support column which can be raised or lowered. Attached to the support column is a cantilevered, curved guide means or support arm which holds and supports the C-arm. By raising and lowering the support column, the doctor, surgeon and/or technician will be able to easily raise or lower the C-arm.

The x-ray electronics may be placed in the cabinet or be placed within a separate support module that is also on wheels and is brought into the room with the scanning equipment.

The C-arm scanner does not pivot in a conventional manner. Rather, the cantilevered, curved guide means is also provided with means for moving the C-arm through a predetermined arcuate path which generally matches the arch of the C-arm. The remaining movement of the C-arm is left to the support column, the underlying first drive wheel, the underlying second drive wheel, and the means for moving the upper chassis relative to the lower chassis.

At the terminal ends of the C-arm are placed an x-ray transmitter and an x-ray receiver, respectively.

During use of the preferred embodiment of this invention, the apparatus can be manually pushed or mechanically driven down a corridor or hallway and into a room of a hospital or clinic to where the patient is laying. As the apparatus approaches the patient and is within the general operable vicinity of the patient, the drive wheel mechanisms are turned to an operational position and are activated. During use of the scanning and/or imaging equipment, the first drive wheel and the second drive wheel have a common, in-line orientation one with another.

Once engaged, the drive wheel mechanisms mechanically propel the apparatus along what is referred to as X-axis. It is intended that the patient be laying upon a table, bed or platform that has a longitudinal axis that is generally parallel to the X-axis of this apparatus. As the scanning and imaging procedure is conducted, the drive wheel mechanisms are activated to move the apparatus and associated scanning and/or imaging means along the X-axis, which is generally parallel to the longitudinal axis of the table, bed or platform.

The worm screw drive or the rack and pinion system can be activated to cause the upper chassis and associated scanner to move in a direction that is generally tangential, perpendicular, or at right angles to the X-axis. We will refer to the movement of the upper chassis relative to the lower chassis as causing the scanner to move within a movable or repositionable Y-axis. In other words, the Y-axis can be moved along the X axis but will remain at a predictable or predetermined tangential, perpendicular, or right angle thereto.

Within the preferred embodiment of this invention, the Y-axis will generally remain at about a ninety degree (90°) angle relative to the X-axis. The X-axis and the Y-axis both generally fall within a horizontal plane.

As briefly explained above, the C-arm scanner has an upright post or support column that can be extended or contracted, or raised and lowered, in a generally vertical manner along a Z-axis. The X-axis and Y-axis are generally tangential, perpendicular, or at right angles to this generally vertical Z-axis.

Consequently, this apparatus permits movement of the scanner within an X-axis, a Y-axis, and a Z-axis. Movement of the scanner along the X-axis is generally in a horizontal plane along the length of the patient laying upon the table, bed or platform. Movement of the scanner along the Y-axis is generally in a horizontal plane either toward or away from the patient laying upon the table, bed or platform, and in a generally tangential orientation with the longitudinal length of the table and patient. Movement of the scanner along the Z-axis is generally in a vertical plane either toward or away from the patient laying upon the table, bed or platform. Furthermore, motion can occur in all three directions at once.

Since the scanner can be easily moved anywhere within the above-stated three-dimensional coordinate system surrounding the patient, the patient need not be positioned or laying within a plane that is perfectly parallel to the foregoing coordinate system of the apparatus. Rather, the apparatus can be manipulated or moved to produce the desired scan of the patient, without moving the patient. During operation of the scanning means, the frame or carriage of this invention precludes any angular motion relative thereto. This is true because all motion and movement of the mobile carriage or lower chassis and the indexing table or upper carriage are always perpendicular with respect to each other. Also, the apparatus can perform multiple motion tasks simultaneously.

In other words, this invention provides unrestrained movement in any direction along the plane of the floor due to the absence of any restricting guides or rails that were heretofore mounted and secured to either the floor or to the ceiling. Floor and/or ceiling mounting is no longer required. Instead, this invention is fully mobile.

Once the scan is performed, the apparatus and its associated scanner can be quickly and easily removed from the room without disturbing or moving the patient.

By controlling the activation and electrical power running to either the first drive motor or to the second drive motor, but not the other, or by operating one drive motor in forward and the other in reverse, the apparatus can be easily rotated and maneuvered.

Within the preferred embodiment of this invention, when assuming their operational positions, the first drive wheel and the second drive wheel are placed or positioned along a common X-axis. Consequently, if there is a discrepancy in the rotational rates of the drive wheels or drive motors, no problems will be created because both wheels share a common path of movement along the X-axis. In other words, by placing these two drive wheel along a common ray or path, potential torsion between the drive wheel is essentially eliminated.

To transport the apparatus down a hallway, corridor or through a room, the drive wheels should be rotated so that the effective width of the apparatus can be minimized during such travel. For example, when the scanner is being wheeled down the hallway, corridor or through the room, the drive wheels can be rotated about ninety degrees (90°) from an operational or operative position to a traveling position. Once secured within their traveling positions, both drive wheels will have a similar but generally parallel path of travel. The third wheel will either lead or trail the two drive wheels.

To accomplish the rotation of one or more of the drive wheels, one or more rotator motors may be used. The rotator motor or motors may be operatively connected to their respective drive wheels via one or more belts, or a rack and pinion system. Within the preferred embodiment of this invention, the rotator motors are connected to their respective drive wheels via a pair of twin timing belts and related caster timing pulleys.

Alternatively, the rotator motor or motors may be operatively connected to their respective drive wheels via a single or plurality of ninety degree gear drives.

When switching between the operational and traveling positions, the inventor prefers to remove and insert or engage and disengage a catch pin, switch, or lockable clutch mechanism. Once the locking mechanism is disengaged, the drive wheel can be easily rotated via activation of the rotator motor and associated belt or rack and pinion system to move the drive wheel between its operational position and its traveling position. Once the desired position is obtained, the locking mechanism is engaged to maintain the accuracy and safety of the apparatus.

Furthermore, each drive motor may be provided with a clutch mechanism. When the clutch mechanisms are deactivated or disengaged, there is no operable connection between the drive motors and the drive wheels. Instead, the apparatus can simply be pushed for transportation.

When the clutch mechanisms are disengaged, the drive wheels can be rotated by one or more electrical rotator motors pulling the wheels, or the structures upon which they are supported, in an arched motion about a pair of generally vertical, parallel, pivotal axes.

Within the preferred embodiment, both drive wheels are pulled or rotated toward each other. The apparatus can then be simply pushed down the hallway. The apparatus, and more particularly the lower chassis or undercarriage, can use a single rotator motor to control the rotation of just one or both of the drive wheels. In other words, each drive wheel ay have its own rotator motor or share a single rotator motor. Pulleys and belts can be used to further accomplish this task.

Within the preferred embodiment of this invention, the drive wheels are disengaged from the powered drive motors and are not powered when placed and secured within their transporting positions. In other words, the drive wheels are disengaged from the drive motors and are not powered when in their transporting positions. To accomplish this task, an engagable and disengagable clutch mechanism may be operatively placed between each drive wheel and their respective drive motors.

Alternatively, the drive wheels can be powered when placed and secured within their transporting position.

The apparatus should be protected from operating room blood, gauze and other debris laying on the floor from entering into the mechanical and electrical components. To protect the apparatus, a bottom plate or protective shield can be used to enclose and generally encapsulate the inner workings of the apparatus.

In addition, rubber, silicon, or other flexible wiper washers or boots may be used adjacent to and/or around the drive wheels and/or around the spherical third wheel to keep out the contaminants and debris from being drawn up into the apparatus. If desired, the wiper washers may rotate with the wheels. When the drive wheels rotate, the debris and contaminants are wiped off.

The preferred and several different alternative embodiments of the apparatus, and associated structures, of the current invention and the processes for manufacture and use thereof are further described in greater detail in the following description, Claims, and drawings of this Specification. However, to avoid any possible confusion as to the scope of the current invention, each of the following sections, claim language, and the drawings of this Specification in their entirety are incorporated within this section by this reference.

The foregoing and other objectives and advantages of the current invention will become more readily apparent upon reading the following disclosure and referring to the attached drawings.

BRIEF DESCRIPTION OF DRAWINGS

FIG. 1A also illustrates in phantom lines the upper chassis and cabinet moved forward to an extended position.

FIG. 2A is a partial, cross-sectional, side-elevational view of a first embodiment this invention, as seen along a plane defined by line II—II in FIG. 1A with the upper chassis, cabinet, controls, and C-arm moved rearward to a retracted position.

FIG. 6 is a partial, plan view of the third embodiment of this invention as shown within FIG. 5, wherein the upper chassis is moved forward to an extended position and the rotator motor has caused the first drive wheel to rotate about a first generally vertical axis from an operative position to a traveling position.

FIG. 7 is an enlarged, partial, side-elevational view of the second drive wheel, means for coupling the second wheel to the lower chassis, and means for selectively rotating the second wheel about a second generally vertical axis between a traveling position and an operational position.

FIG. 8 is an enlarged, partial, end-elevational view of the second drive wheel and means for mechanically or electrically rotating the second drive wheel in a selectively controlled manner about the second generally horizontal axis, by means of using a second drive motor that is operatively and/or directly secured to the lower chassis.

FIG. 9 also illustrates means for mechanically or electrically moving the upper chassis in a selective and controlled manner along a predetermined path relative to the lower chassis between a closed or retracted position and an extended position as comprising a worm-screw operatively secured to the upper chassis, a drive nut operatively secured to the lower chassis and operatively engaged with the worm-screw, and a scanner motor operatively connected to the worm-screw to selectively rotate the worm-screw in a predetermined and controlled manner.

Figure 1A:
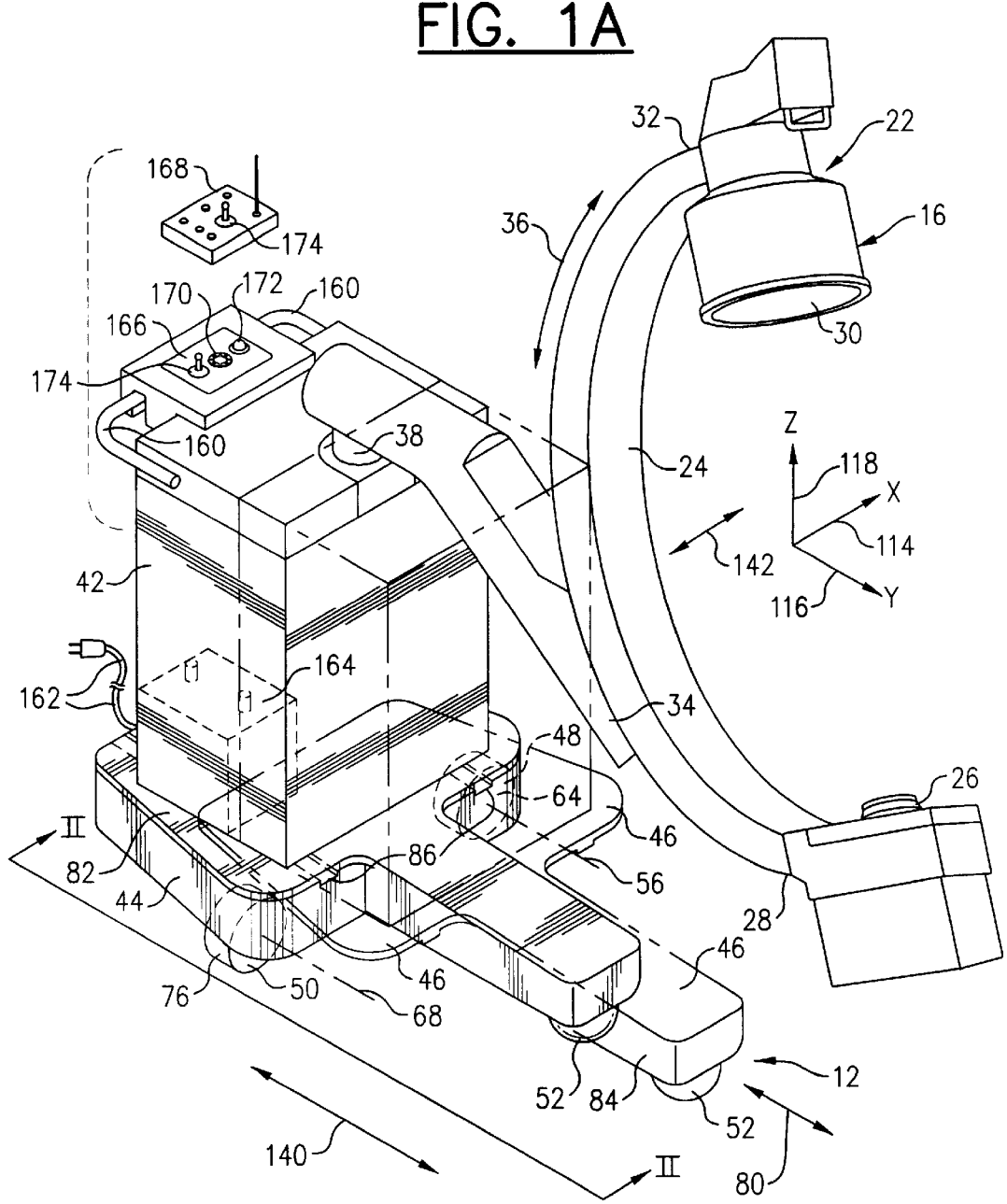
FIG. 1A is a perspective view of a first embodiment of the current invention, made in accordance with the teachings of this disclosure, using solid lines to illustrate the upper chassis, lower chassis, cabinet, controls, handle, and C-arm in a retracted position.

One should understand that the drawings are not necessarily to scale and the elements are sometimes illustrated by graphic symbols, phantom lines, diagrammatic representations, and fragmentary views. In certain instances, details which are not necessary for an understanding of the current invention or which render other details difficult to perceive may be omitted.

BEST MODE FOR CARRYING OUT THE INVENTION

Referring to the drawings, wherein like numerals indicate like parts, the current invention includes an apparatus 12, which is placed upon and is supported by an underlying floor 14. The apparatus 12 is used to transport and control at least a portion of the operational movement of means 16 for conducting medical scans and/or images, or in other words, medical scanning equipment, about a portion of a body of a patient. For example, the apparatus 12 may be used to transport and/or control the movement of mobile x-ray-imaging, angiogram, thermal-imaging, ultrasonic-imaging, magnetic-resonance-imaging, and/or any other type of medical scanning and/or imaging equipment.

The apparatus 12 is intended to significantly improve the ease and ability to gather medical data, and to dramatically increase the accuracy of such data. For example, the apparatus 12 can be used to assist in conducting: angiography, digital subtraction angiography (DSA), interventional, endovascular, catheterization, neurological, vascular, cardiac, trauma, internal, endoscopy, fluoroscopy, and urology procedures; endoluminal grafting; bone studies; medical roadmapping; maximal opacification; and assist in many other static and/or dynamic applications.

While conducting the medical procedure, the apparatus 12 can actively and progressively move the scanning and/or imaging means 16 or equipment about at least a portion of a body 18 of a patient 20 without having to manhandle the apparatus 12 to a new position to scan or register each new image. In other words, the scanning and/or imaging means 16 can be moved along at any desired speed and moved to nearly any desired location about the body 18 of the patient 20 without having to stop the medical procedure or move the patient 20. Consequently, the speed and accuracy of the data gathered are significantly higher than heretofore thought possible. Furthermore, due to the rapid gathering and high quality of such information, the fluoroscopic dose level required to be given to the patient 20 can be minimized.

Within the illustrated preferred and alternative embodiments of this invention, the scanning and/or imaging means 16 or equipment generally comprises a mobile x-ray device 22 having a C-arm 24 which carries a transmitter 26 at a first end 28 thereof and a receiver 30 at an opposed second end 32.

The C-arm 24 is supported by a cantilevered, curved guide means 34 that is capable of guiding and advancing the scanning and/or imaging means 16, i.e., the transmitter 26 and the receiver 30, through a predetermined curved path 36.

Figure 1B:
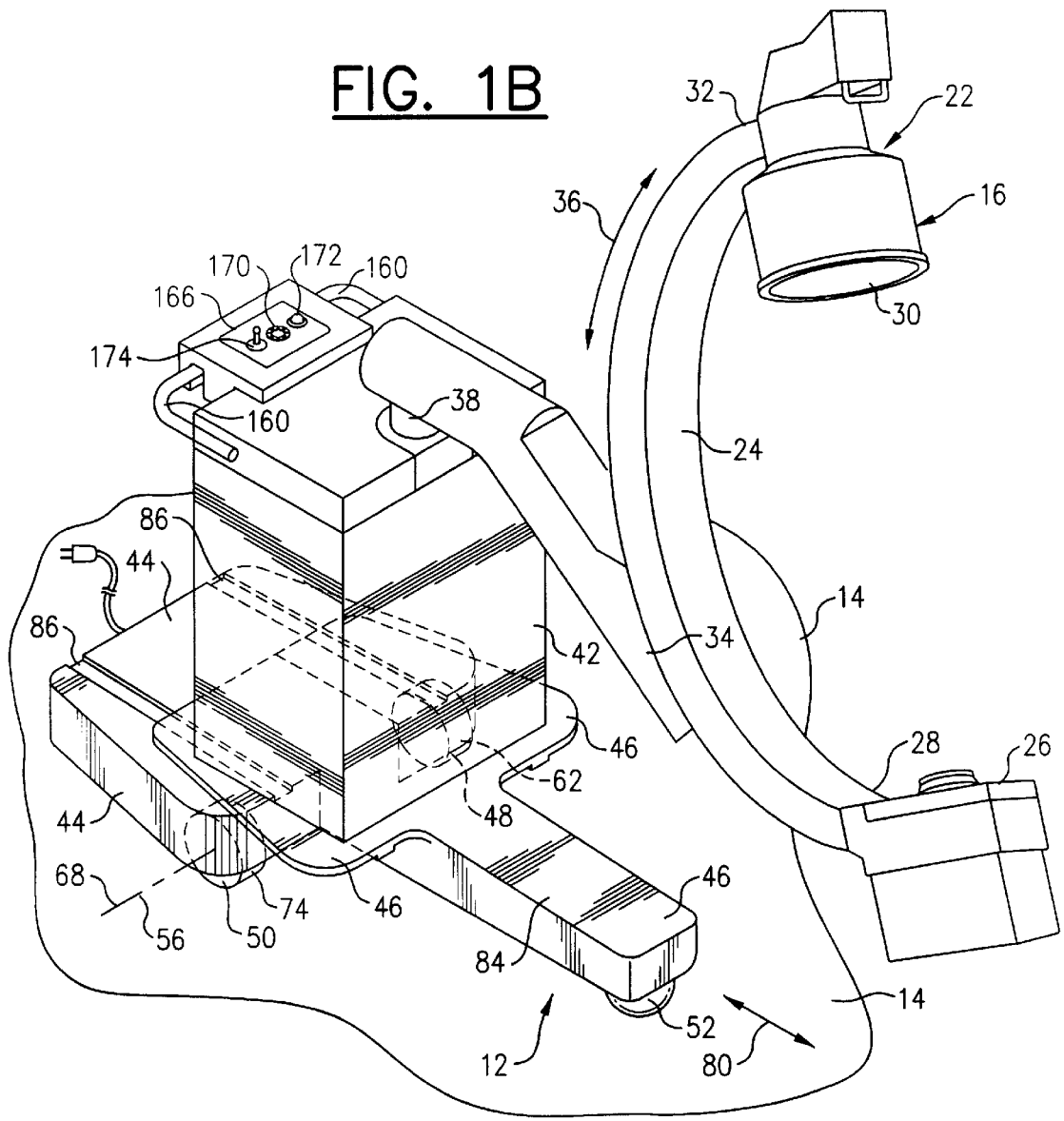
FIG. 1B is a perspective view of the first embodiment of this invention illustrating the upper chassis, cabinet, controls, and C-arm in an extended position.
Figure 2B:
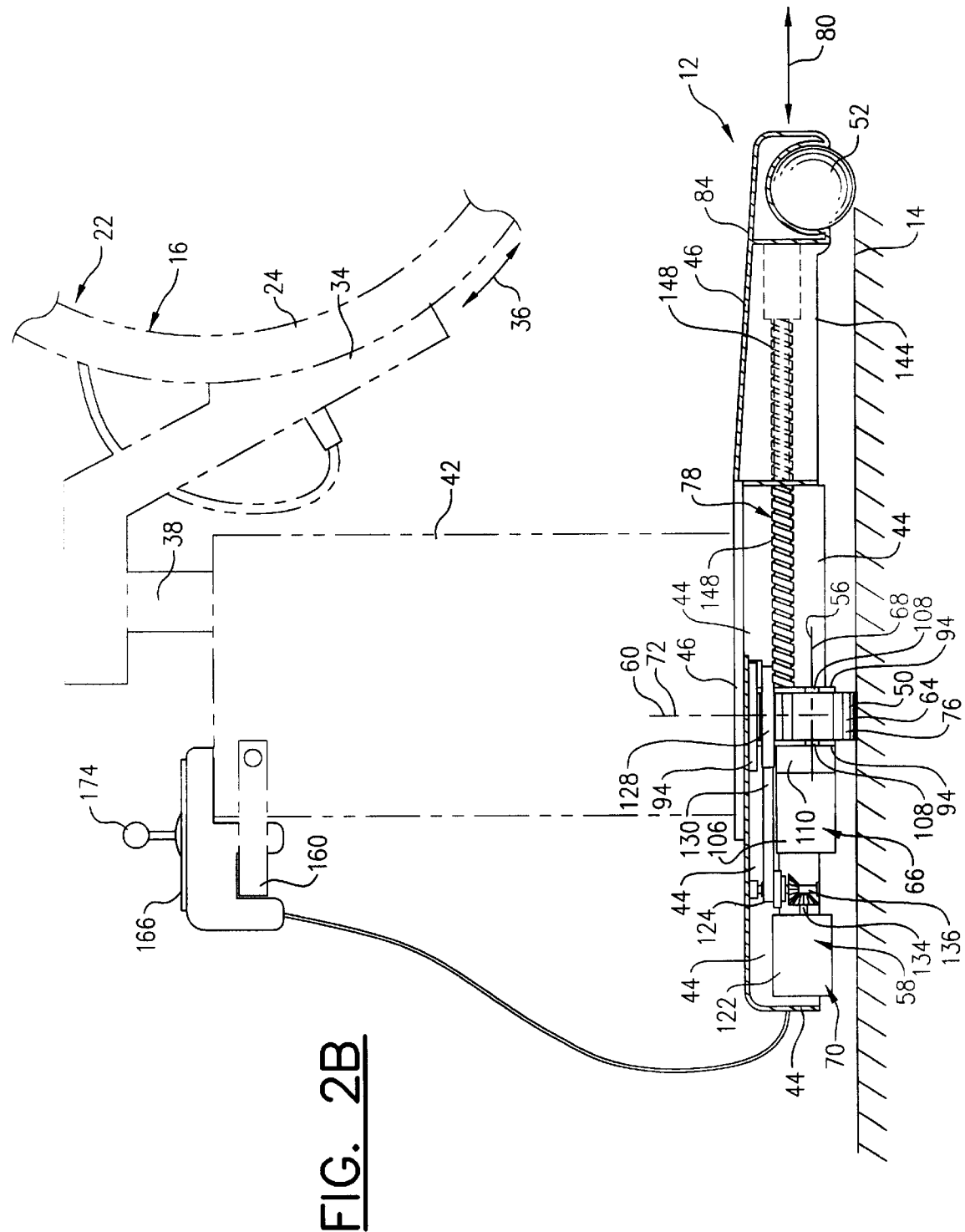
FIG. 2B is an enlarged, partial, cross-sectional, side-elevational view of the first embodiment this invention, as seen along a plane defined by line II—II in FIG. 1A with the upper chassis, cabinet, controls, and C-arm moved forward to an extended position.
Figure 2C:
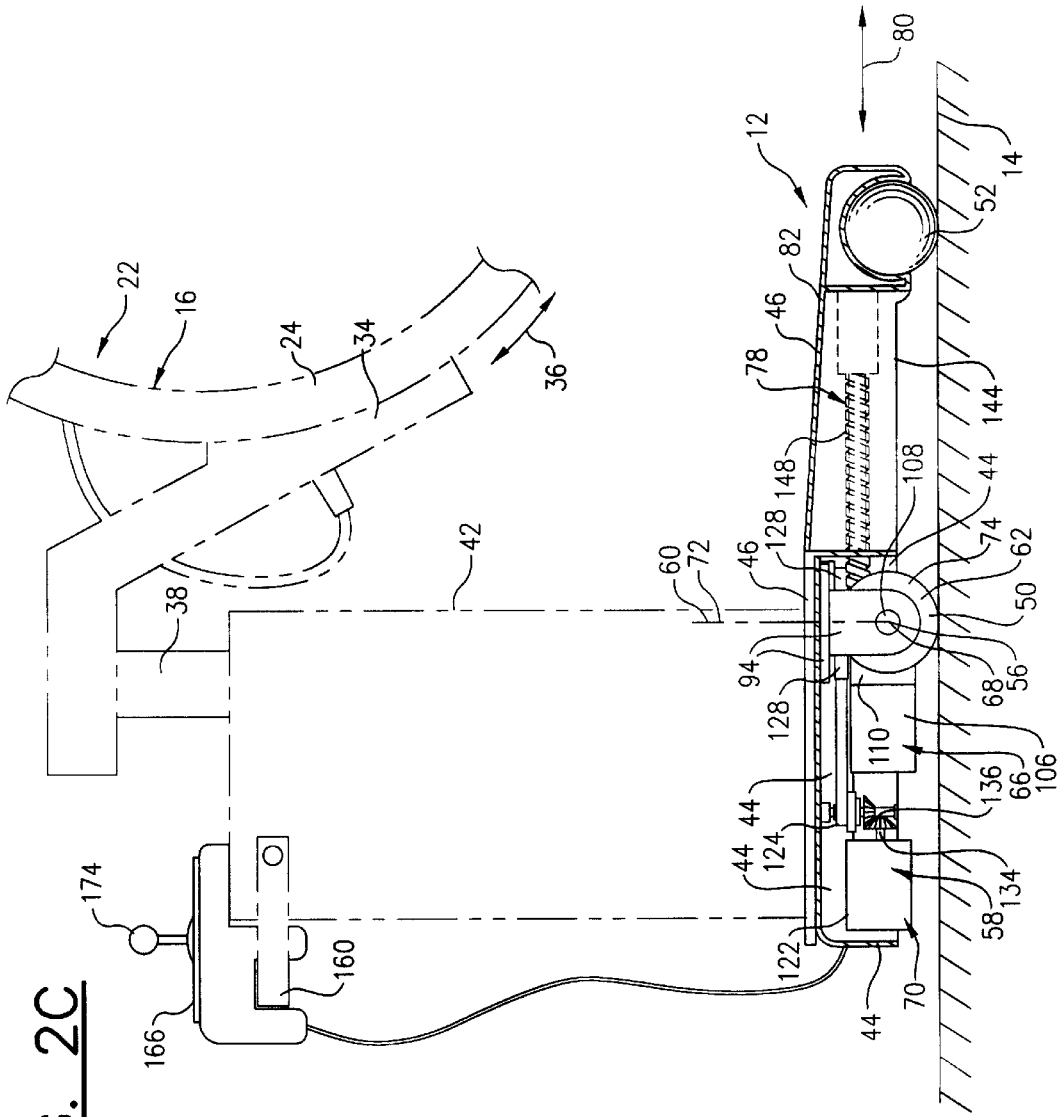
FIG. 2C is an enlarged, partial, cross-sectional, side-elevational view of the first embodiment this invention, as seen along a plane defined by line II—II in FIG. 1A with the upper chassis, cabinet, controls, and C-arm moved rearward to a closed or retracted position.

The cantilevered, curved guide means 34 is supported by a support column 38 that has a generally vertical orientation. Support column 38 can be selectively raised or lowered to position, adjust and/or modify the height of the curved guide means 34 and, as a consequence, the height of the scanning and/or imaging means 16 relative to the floor 14 and relative to the patient 20. FIGS. 1A, 1B and 2A illustrate the support column 38 in a generally lowered position. FIGS. 2B and 2C illustrate the support column 38 in a generally raised position. Of course the indicated height is not limiting in this invention. Any desired height can be achieved.

Typically, the patient 20 lays upon a transparent, translucent, radiolucent, carbon-fiber, glass and/or plastic, cantilevered table 40 which has an approximately horizontal orientation. Preferably, the table 40 is cantilevered from a fixed support structure 41 such as a wall, the floor 14, or a separate support stand.

Radiation emitted by the transmitter 26 of the scanning and/or imaging means 16 is permitted to pass through the table 40 and the patient 20 and be received into the receiver 30.

Electrical equipment necessary to operate and to raise and/or lower the scanning and/or imaging means 16 is preferably contained within a cabinet 42. Cabinet 42 is preferably positioned below and adjacent to the support column 38.

An ideal scanning and/or imaging means 16 that has many of the above-listed features, i.e., the C-arm 24, the transmitter 26, the receiver 30, the curved guide means 34, support column 38, and cabinet 42, is the BV212 mobile x-ray unit sold by Philips Medical Systems. Of course, other scanning and/or imaging means 16 or equipment could be used.

The apparatus 12 of the preferred embodiment of this invention is intended to be used with the above-described scanning and/or imaging means 16. In essence, the apparatus 12 comprises the combination of: (a) a lower chassis 44; (b) an upper chassis 46; (c) a first drive wheel 48; (d) a second drive wheel 50; (e) a third wheel 52; (f) means 54 for mechanically or electrically rotating the first wheel 48 about a first generally horizontal axis 56 in a selectively controlled manner; (g) means 58 for selectively rotating the first wheel 48 about a first generally vertical axis 60 between a first traveling position 62 and a first operational position 64; (h) means 66 for mechanically or electrically rotating the second wheel 50 about a second generally horizontal axis 68 in a selectively controlled manner; (i) means 70 or 70' for selectively rotating the second wheel 50 about a second generally vertical axis 72 between a second traveling position 74 and a second operational position 76; and (j) means 78 for mechanically or electrically moving the upper chassis 46 in a selective and controlled manner along a predetermined path 80 relative to the lower chassis 44 between a retracted position 82 and an extended position 84.

The lower chassis 44 is positioned above but adjacent to the underlying floor 14.

The upper chassis 46 is operatively and movably secured to the lower chassis 44. For example, the lower chassis 44 may be provided with one or more tracks 86, grooves, slots, or indentations into which at least a portion of the upper chassis 46 is operatively and movably secured. If desired, the tracks 86 may comprise a pair of sealed ball slide tracks, having ball rails and linear bearings that are mounted parallel to each other. The linear bearings are attached to the bottom of the upper chassis 46 allowing the upper chassis 46 to move along a single plane of motion above the surface of the lower chassis 44.

Similarly, the tracks 86 may comprise one or more V-tracks and corresponding V-wheel slides.

Activation of the first drive wheel 48 and the second drive wheel 50 provides for motion of the apparatus 12 along the length of the examination table 40. The upper chassis 46 or indexing table is mounted in such a way as to provide motion towards and away from the side of the table 40, which is perpendicular to the plane of motion of the lower chassis 44.

The first drive wheel 48 is operatively secured to the lower chassis 44. More particularly, the apparatus 12 comprises means 88 for coupling the first wheel 48 to the lower chassis 44. The first coupling means 88 enables the first wheel 48 to rotate about the first generally horizontal axis 56 and enables the first wheel 48 to rotate about the first generally vertical axis 60.

Similarly, the second wheel 50 is also operatively secured to the lower chassis 44. The apparatus 12 includes means 94 for coupling the second wheel 50 to the lower chassis 44. The second coupling means 94 enables the second wheel 50 to rotate about the second generally horizontal axis 68 and enables the second wheel 50 to rotate about the second generally vertical axis 72.

The first wheel 48 and the second wheel 50 are arranged to at least partially support the lower chassis 44 upon the floor 14 and enable movement of the lower chassis 44 relative to the floor 14.

The third wheel 52 is operatively secured to the upper chassis 46. The third wheel 52 preferably comprises a rotatable and omnidirectional wheel. Consequently, the first wheel 48 and the second wheel 50 can be used to steer the apparatus 12 without the third wheel 52 dragging along or skidding against the floor 14. In other words, the third wheel 52 permits movement of the lower chassis 44 and the upper chassis 46 in any direction that is generally parallel to or horizontal with the floor 14. The third wheel 52 also permits movement of the upper chassis 46 relative to the lower chassis 44 between the retracted position 82 and the extended position 84 and provides additional support and stability to the upper chassis 46 when doing so. More particularly, as the upper chassis 46 is moved toward its extended position 84, the third wheel 52 also moves to an extended position and remains below the C-arm 24. Consequently, there will be no danger that extension of the upper chassis 46 and/or C-arm 24 will cause the apparatus 12 to tip over due to an excessive change in the center of gravity of the apparatus 12. The center of gravity will always remain between the third wheel 52, the first drive wheel 48, and the second drive wheel 50.

In essence, the first wheel 48, the second wheel 50, and the third wheel 52 form a tripod upon which the remaining portions of the apparatus 12 are supported and upon which the apparatus 12 is moved and transported across the floor 14.

As stated above, the apparatus 12 is provided with the means 54 for mechanically or electrically rotating the first wheel 48 in a selectively controlled manner about the first generally horizontal axis 56. Such first rotating means 54 preferably comprises a first drive motor 100 that is secured to the lower chassis 44. The first drive motor 100 is secured to the lower chassis 44 in such a manner as to prevent rotation of a housing of the first drive motor 100 relative thereto. A drive shaft 102 of the first drive motor 100 is operatively and/or directly connected to the first wheel 48.

If desired, a first clutch mechanism 104 may be operatively secured between the first drive motor 100 and the first wheel 48. The first clutch mechanism 104 can be used to disengage or engage the first wheel 48 with the first drive motor 100. For example, if desired, the first wheel 48 can be disengaged from the first drive motor 100 when the apparatus 12 is being pushed down a corridor or hallway. Once the apparatus 12 is placed near to the patient 20, the first clutch mechanism 104 can be activated to engage the first wheel 48 with the first drive motor 100 for motorized operation of the apparatus 12 during the medical procedure.

The apparatus 12 should also be provided with means 66 for mechanically or electrically rotating the second wheel 50 in a selectively controlled manner about the second generally horizontal axis 68. Second rotating means 66 may comprise a second drive motor 106 that is operatively secured to the lower chassis 44.

A second drive motor 106 can be directly or indirectly connected to the second wheel 50. Of course, the second drive motor 104 would be secured to the lower chassis 44 in such a manner as to prevent rotation of a housing of the second drive motor 104 relative thereto. A drive shaft 108 of the second drive motor 106 is operatively and/or directly connected to the second wheel 50.

If desired, a second clutch mechanism 110 may be operatively secured between the second drive motor 106 and the second wheel 50. The second clutch mechanism 110 can be used to disengage or engage the second drive wheel 50 to the second drive motor 106. For example, if desired, the second drive wheel 50 can be disengaged from the second drive motor 106 when the apparatus 12 is being pushed down a corridor or hallway. Once the apparatus 12 is placed near to the patient 20, the second clutch mechanism 110 can be activated to engage the second drive wheel 50 with the second drive motor 106 for motorized operation of the apparatus 12 during the medical procedure.

If desired the first clutch mechanism 104 and the second clutch mechanism 110 can be activated or deactivated in unison, concurrently, or simultaneously. To accomplish this task, as shown within FIGS. 5, 6, 9 and 10, a proximity or electrical switch 112 can be secured to the lower chassis 44. In other words, mechanical rotation of the first drive wheel 48 and of the second drive wheel 50 are stopped by the contact and actuation of the electrical limit switch 112 or switches.

FIGS. 1, 2, 3, 5 and 8, illustrate the first drive wheel 48 assuming its first operational position 64 and the second drive wheel 50 assuming its second operation position 76. In these positions, the first clutch mechanism 104 is engaged to the first drive motor 100, and the second clutch mechanism 110 is engaged to the second drive motor 106. The first drive wheel 48 and the second drive wheel 50 are both oriented to move along an X-axis 114 as required during performance of the medical procedure.

FIGS. 6, 7 and 8, illustrate the first drive wheel 48 assuming a first traveling position 62 and the second drive wheel 50 assuming a second traveling position 74. In these positions, the first clutch mechanism 104 can be disengaged from the first drive motor 100 and the second clutch mechanism 110 can be disengaged from the second drive motor 106. The first drive wheel 48 and the second drive wheel 50 are both oriented to move along a Y-axis 116 and are positioned for traveling and not positioned for performance of the medical procedure.

Please also recall that the support column 38 permits the scanning and/or imaging means 16 to move upwardly and downwardly along a Z-axis 118.

The apparatus 12 also includes means 58 for selectively rotating the first drive wheel 48 about the first vertical axis 60 between the first traveling position 62 and the first operational position 64. For example, rotating means 58 may comprise: (a) a first pulley 120 that is operatively secured to the first coupling means 88; (b) a mechanically or electrically powered first rotator motor 122 that is operatively secured to the lower chassis 44; (c) a second pulley 124 that is operatively secured to the first rotator motor 122; and (d) a first drive belt 126 that is operatively secured to and positioned between the first pulley 120 and the second pulley 124.

The means 70 for selectively rotating the second drive wheel 50 about the second generally vertical axis 72 between the second traveling position 74 and the second operational position 76 may similarly comprise: (a) a third pulley 128 that is operatively secured to the second coupling means 94; and (b) a second drive belt 130 that is operatively secured to and positioned between the third pulley 128 and the second pulley 124. Thus positioned, the first rotator motor 122 can be used to rotate both the first drive wheel 48 and the second drive wheel 50. This embodiment is illustrated within FIGS. 2A, 2B and 2C.

Alternatively, as illustrated within FIGS. 5, 6, 7 and 8, the second rotating means 70 for selectively rotating the second drive wheel 50 about the second generally vertical axis 72 between the second traveling position 74 and the second operational position 76 may further include a fourth pulley 132 which is also operatively connected or journaled to the first rotator motor 122. This alternative embodiment is illustrated within FIG. 5.

In essence, rotation of a drive shaft 134 transmits power either directly to or through the engagement of one or more bevel gears 136 to rotate both the second pulley 124 and the fourth pulley 132. In turn, the second pulley 124 drives and rotates the first drive belt 126, which rotates the first pulley 120, the first coupling means 88, and the first drive wheel 48. Similarly, the fourth pulley 132 drives and rotates the second drive belt 130, which rotates the third pulley 128, the second coupling means 94, and the second drive wheel 50. Please note that second drive belt 130 may or may not be crossed over itself, depending upon the particular structure used within the bevel gears 136. Furthermore, if desired, a reduction gear crankcase can be used within the bevel gears 136.

Figure 9:
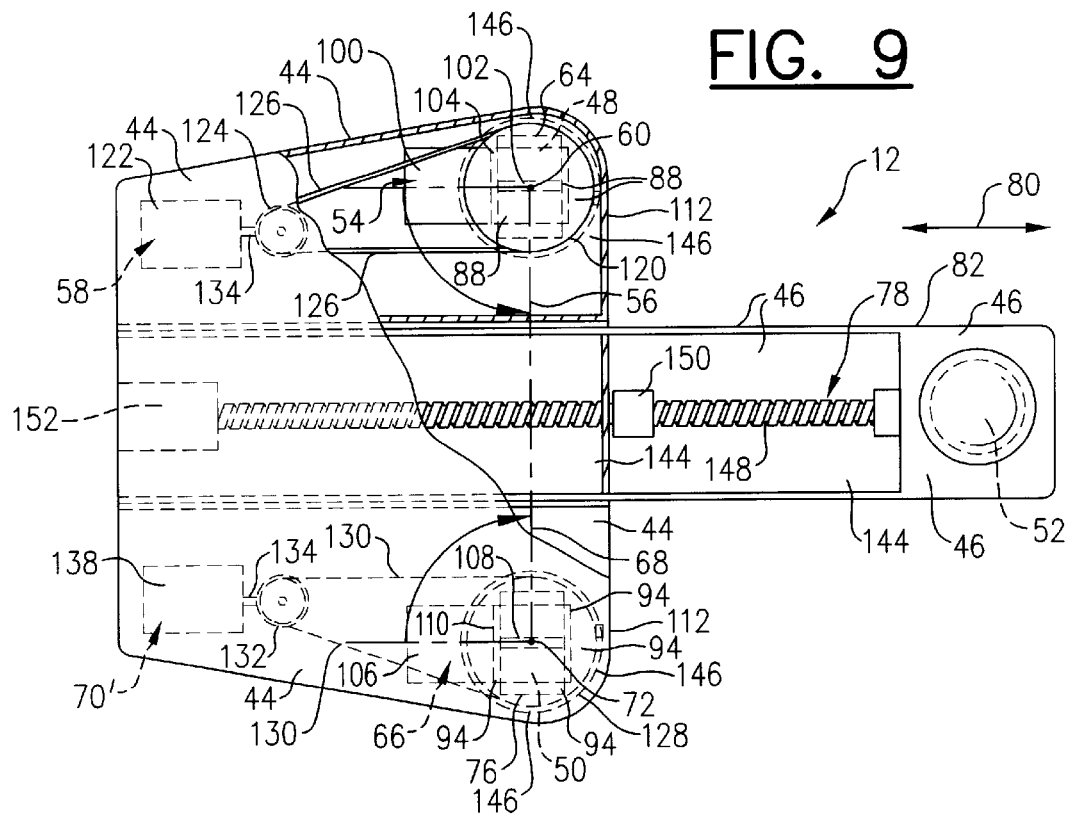
FIG. 9 is a partial, plan view of a fourth embodiment of this invention, wherein a first drive wheel is provided with a first rotator motor and a second drive wheel is provided with a second rotator motor.
Figure 10:
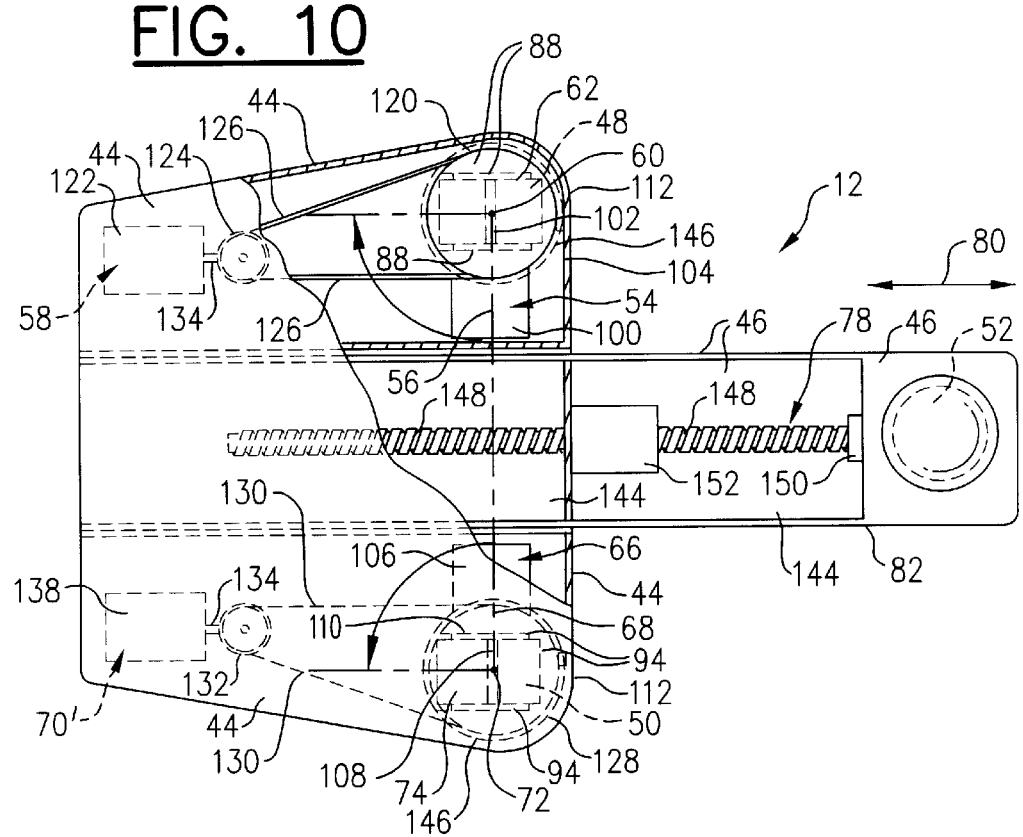
FIG. 10 is a partial, plan view of a fifth embodiment of this invention which is very similar to the fourth embodiment shown within FIG. 9. However, within the fifth embodiment of this invention, the worm-screw is operatively secured to the lower chassis, the drive nut is operatively secured to the upper chassis, and the scanner motor is operatively connected to the worm-screw to rotate the worm-screw.

A further alternative embodiment is illustrated within FIGS. 9 and 10, wherein the first drive wheel 48 is provided with its own first rotator motor 122, and the second drive wheel 50 is provided with its own independent second rotator motor 138. Within this embodiment, the third pulley 128 is operatively secured to the second coupling means 94 as described above. A mechanically or electrically powered second rotator motor 138 is operatively secured to the lower chassis 44. The fourth pulley 132 is operatively secured to the second rotator motor 138. The second drive belt 130 is operatively secured to and positioned between the third pulley 128 and the fourth pulley 132.

Rotation of a drive shaft 134 on second rotator motor 138 transmits power either directly to or through the engagement of one or more bevel gears 136 to rotate the fourth pulley 132. In turn, the fourth pulley 132 drives and rotates the second drive belt 130, which rotates the third pulley 128, the second coupling means 94, and the second drive wheel 50.

As explained above, the lower chassis 44 moves along a first path 140, which is generally parallel to the Y-axis 116, when the first drive wheel 48 is in its first traveling position 62 and the second drive wheel 50 is in its second traveling position 74.

However, the lower chassis moves along a second path 142, which is generally parallel to the X-axis 114, when the first drive wheel 48 is in its first operational position 64 and the second drive wheel 50 is in its second operational position 76.

The first traveling position 62 and first path 140 is intended to be generally tangential or perpendicular to the first operational position 64 and second path 142.

Similarly, the second traveling position 74 and is intended to be generally tangential or perpendicular to the second operational position 76.

Furthermore, the first drive wheel 48, the first rotating means 54, the second drive wheel 50, and the second rotating means 66 should be capable of moving the lower chassis 44 in a very precise, predictable, and regulated manner.

If desired, the apparatus 12 may include a protective shield 144 that is secured to the lower chassis 44 to shield the lower chassis 44 from drawing in contaminants and/or debris therein.

The apparatus 12 may also comprise at least one wiper blade 146 or washer secured to the lower chassis 44 about the first drive wheel 48, the second drive wheel 50, and/or the third wheel 52 to further shield the lower chassis 44 from drawing in contaminants and/or debris therein.

Figure 5:
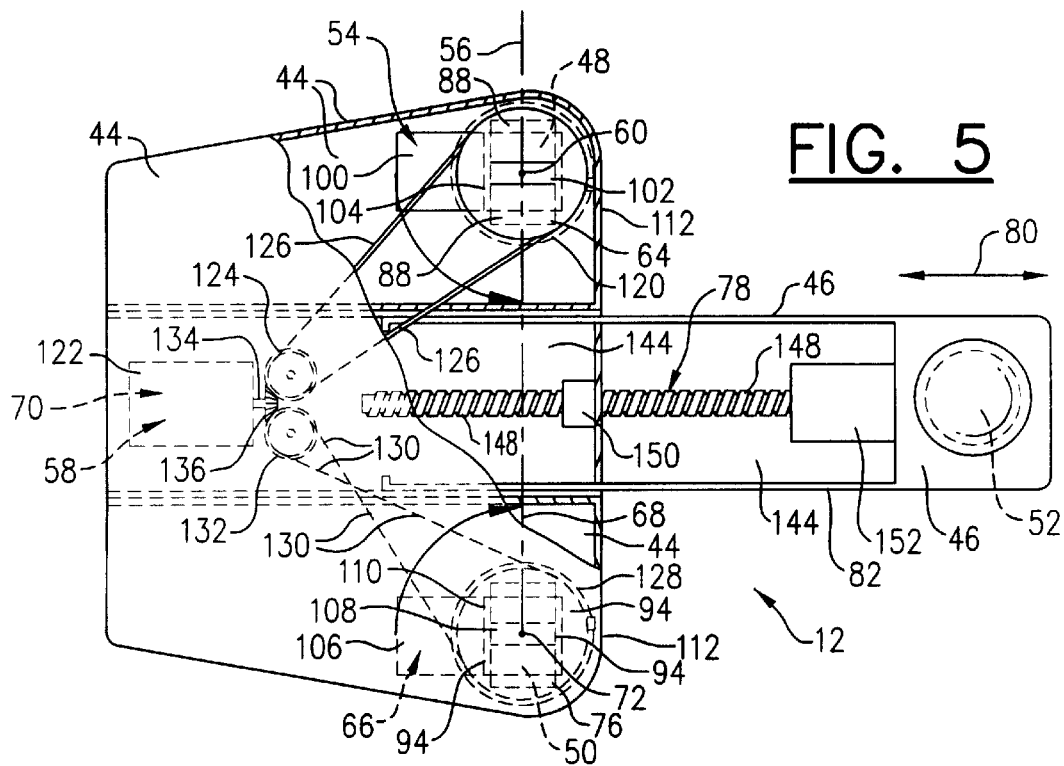
FIG. 5 is a partial, plan view of a third embodiment of this invention, wherein a single rotator motor is used to rotate the first drive wheel and the second drive wheel, and the upper chassis is in a closed or retracted position.

As best seen within FIGS. 5 and 6, the means 78 for mechanically or electrically moving the upper chassis 46 in a selective and controlled manner along the predetermined path relative to the lower chassis 44 between the retracted position 82 and the extended position 84 may include use of: (a) a worm-screw 148 that is operatively secured to the upper chassis 46; (b) a drive nut 150 that is operatively secured to the lower chassis 44 and is operatively engaged with the worm-screw 148; and (c) a scanner motor 152 that is operatively connected to the worm-screw 148 and to the upper chassis 46 to selectively rotate the worm-screw 148 in a predetermined and controlled manner. More particularly, the rotary motion of the worm screw 148 translates to linear motion via the drive nut 150 or a ball screw and recirculating ball nut assembly. For example, the ball screw or worm screw 148 could be mounted to the top of the lower chassis 44, between and generally parallel to the linear ball rails or tracks 86. The worm screw 148 is thus mounted via use of pillow block bearings which are attached to each end of the worm screw 148 in such a way as to capture the worm screw 148 axially, yet allow unlimited rotary motion of the worm screw 148. The ball screw or worm screw 148 threads through the ball nut in such a way as to cause the ball nut to move forward and back along the length of the worm screw 148 as the worm screw is rotated. With the recirculating ball nut being fixed to the underside of the movable upper chassis 46, the rotation of the worm screw 148 causes the upper chassis 46 to move forward and backward depending upon the direction of rotation of the worm screw 148.

Alternatively, as best seen within FIGS. 9 and 10, the means 78 for mechanically or electrically moving the upper chassis 46 in a selective and controlled manner along the predetermined path relative to the lower chassis 44 between the retracted position 82 and the extended position 84 may include use of: (a) a worm-screw 148 that is operatively secured to the lower chassis 44; (b) a drive nut 150 that is operatively secured to the upper chassis 46 and is operatively engaged with the worm-screw 148; and (c) a scanner motor 152 that is operatively connected to the worm-screw 148 and to the lower chassis 44 to selectively rotate the worm-screw 148 in a predetermined and controlled manner. The position of the scanner motor 152 relative to the lower chassis 44 is not determinative. For example, FIG. 9 illustrates the scanner motor 152 secured to the lower chassis 44 at a rearward position. However, FIG. 10 illustrates the scanner motor 152 secured to the lower chassis 44 at a different and forward position.

Figure 3:
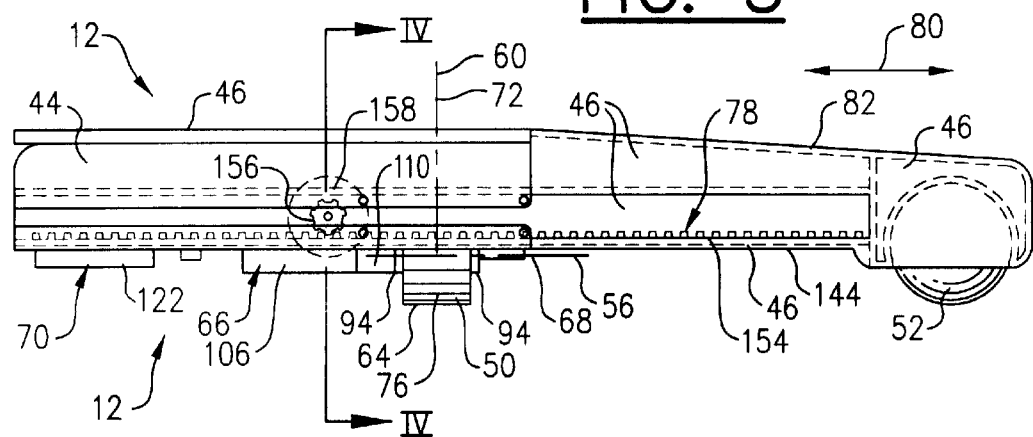
FIG. 3 is a partial, cross-sectional, side-elevational view of an upper chassis and a lower chassis of a second embodiment of this invention, somewhat similar to the illustrations of FIGS. 2A and 2B. However, instead of using a worm-screw mechanism to advance and retract the upper chassis relative to the lower chassis, a rack and pinion mechanism is illustrated and used.
Figure 4:
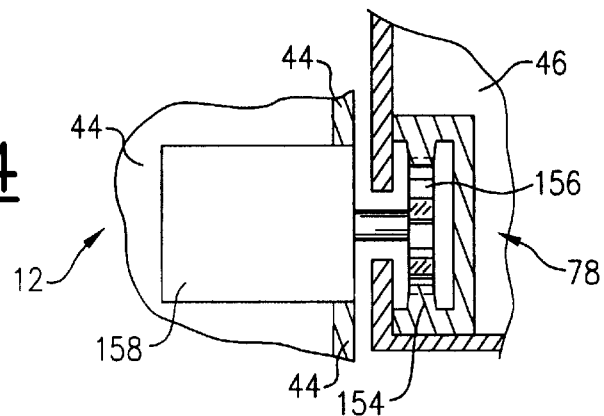
FIG. 4 is an enlarged, partial, cross-sectional, end-elevational view of the rack and pinion mechanism as seen along a plane defined by line IV—IV in FIG. 3.

As illustrated within FIGS. 3 and 4, the means 78 for mechanically or electrically moving the upper chassis 46 in a selective and controlled manner along the predetermined path relative to the lower chassis 44 between the retracted position 82 and the extended position 84 may include use of a rack 154 and pinion 156 system. For example, the rack 154 may be operatively secured to the upper chassis 46. The pinion 156 or toothed gear is operatively secured to a powered rack and pinion drive motor 158, which in turn is operatively secured to the lower chassis 44. Teeth on the pinion 156 engage corresponding teeth on the rack 154 to move the upper chassis 46 back and forth along the Y-axis in a predetermined and controlled manner.

Within the preferred embodiment of this invention, the cabinet 42 is either operatively secured to the apparatus 12 or is incorporated therein. More particularly, the cabinet 42 is either operatively secured to the upper chassis 46 or is incorporated therein.

The cabinet 42 may be provided with a handle 160 which is secured thereto. The handle 160 can be used to help and assist in steering, pushing and/or pulling the apparatus 12 along a corridor or hallway.

Of course the various motors included within this invention can be selectively powered. As shown within FIG. 1A, an electrical chord 162 can be plugged into a conventional electrical power outlet to provide electrical power to such motors.

Alternatively, one or more batteries 164 could be operatively connected to such motors to provide electrical power thereto. For example, the batteries 164 could be transported and stored within the cabinet 42 as shown within FIG. 1A.

To operate and control the various motors within the apparatus 12, the cabinet 42 may be provided with a permanently installed control panel 166. Alternatively, or in addition thereto, a hand-held control panel 168 may also be provided. Control panel 166 and/or control panel 168 may be used to activate and/or deactivate the scanning and/or imaging means 16, the transmitter 26, the curved guide means 34, the raising and lowering of the support column 38, the rotating means 54, the rotating means 58, the rotating means 66, the rotating means 70, and the moving means 78. More particularly, the control panel 166 and/or control panel 168 may be used to activate and/or deactivate such elements as: the first drive motor 100, the first clutch mechanism 104, the second drive motor 106, the second clutch mechanism 110, the first rotator motor 122, the second rotator motor 138, the scanner motor 152, and/or the rack and pinion drive motor 158.

In addition, the receiver 30 or image intensifier can be secured to the C-arm 24 in such a manner as to enable its position to be adjusted. For example, the source to image distance between the transmitter 26 or x-ray tube and the receiver 30 can be variable and adjustable.

The control panel 166 and/or control panel 168 may include a traditional computer keyboard, a specially designed keyboard 170 having directional keys thereon, a computer pointing device, a rotating ball 172 similar to that of a computer mouse, and/or a computer joystick 174.

The control panel 168 is preferably a handle-held control unit that is either remotely controlled, via an elongated attached electrical chord, is radio controlled, and/or is infrared controlled. By using a remote, radio, and/or infrared controlled control panel 168, an operator can stand adjacent to the patient or at a distance, depending upon the needs of the particular medical procedure.

The means and construction disclosed herein are by way of example and comprise primarily the preferred and several alternative forms of putting the invention into effect. Although the drawings depict the preferred and several alternative embodiments of the invention, other embodiments are described within the preceding and following text. One skilled in the art will appreciate that the disclosed apparatus and devices may have a wide variety of designs, shapes, and configurations. Additionally, persons skilled in the art to which the invention pertains might consider the foregoing teachings in making various modifications, other embodiments, and alternative forms of the invention.

It is, therefore, to be understood that this invention is not limited to the particular embodiments or specific features shown herein. To the contrary, the invention is claimed in all of its various forms, including all alternatives, modifications, equivalents, and alternative embodiments that fall within the legitimate and valid scope of the Claims, appropriately interpreted under the Doctrine Of Equivalents.

INDUSTRIAL APPLICABILITY

This invention may be used by any surgeon, doctor, nurse, technician, or other person who is licensed and/or authorized to operate medical scanning equipment. For example, the apparatus and methods of this invention may be used within hospitals, clinics, nursing homes, doctor's offices, military field hospitals, and the like. In essence, the present invention may be used by any person who could benefit from the simple, reliable, easily used apparatus and methods that this invention provides. The apparatus of this invention is compact, unobtrusive, efficient, reusable, durable, rugged, is easily constructed, and is inexpensive and economical to manufacture.

Traditional or nontraditional manufacturing equipment and procedures may be used to manufacture the apparatus of this invention without requiring significant alteration thereto to accomplish the purposes taught herein.

Once manufactured, the apparatus of this invention can be easily transported, used, and stored using a minimum amount of operational and storage space. Consequently, the invention also minimizes the size and cargo space required to contain and ship the apparatus. This in turn, reduces transportation and storage costs.

The current invention has a special benefit of being able to incorporate therein mass produced and commercially available medical scanning equipment and machinery that are readily purchasable at medical supply dealers throughout the world. Furthermore, since mass produced medical scanners can be used, the manufacturer of this invention can purchase such scanning equipment and replacement parts related thereto at very competitive prices.

The base, cart, carriage, or support of this invention can be used with a wide variety of different medical scanning equipment. Consequently, it is anticipated that the potential consumer base for this invention will be significantly broader than what would have been available for the heretofore known devices. The scope and versatility of the present invention is also much broader than the previously known devices.

Although the invention has a wide range of applications, the invention has special application within interventional and/or endovascular procedures. The present invention permits such procedures to be accomplished in multiple rooms. This invention requires that only a minimum amount of effort be exerted to initially position the apparatus adjacent to the patient. Thereafter, the operator will have nearly unlimited ability to move the medical scanning equipment toward or away from the patient, back and forth along the length of the patient, and above, below and around the patient in a nearly unlimited range of orientations with respect to the patient. This invention increases the speed and accuracy and simplifies the methods required to perform such medical procedures. This in turn provides a greater degree of accuracy and reliability in the gathered data upon which the medical professional will stake his or her reputation, with less complications for the user, and is safer for the patient.

Ease and convenience in use is dramatically increased over the prior known devices. The complexity of the apparatus as compared to the prior known devices is greatly reduced. The bulkiness of the apparatus can be minimized to create a streamlined easily cleaned and sanitized apparatus.

We claim:

1. An apparatus supportable upon a floor for moving medical scanning equipment about a portion of a body of a patient, said apparatus comprising a combination of:

(a) a lower chassis positioned above the floor;

(b) a first wheel operatively secured to said lower chassis, said first wheel capable of being rotated about a first generally horizontal axis and a first generally vertical axis;

(c) a second wheel operatively secured to said lower chassis, said second wheel capable of being rotated about a second generally horizontal axis and a second generally vertical axis, said first wheel and said second wheel arranged to support said lower chassis upon the floor and enable movement of said lower chassis relative to the floor;

(d) remotely actuated means for selectively rotating said first wheel about said first vertical axis between a first traveling position and a first operational position, said first traveling position being generally tangential or perpendicular to said first operational position;

(e) remotely actuated means for selectively rotating said second wheel about said second vertical axis between a second traveling position and a second operational position, said second traveling position being generally tangential or perpendicular to said second operational position;

(f) remotely actuated means for mechanically or electrically rotating said first wheel about said first horizontal axis in a selectively controlled manner;

(g) remotely actuated means for mechanically or electrically rotating said second wheel about said second horizontal axis in a selectively controlled manner, said lower chassis moving along a first path when said first wheel is in said first traveling position and said second wheel is in said second traveling position, said lower chassis moving along a second path when said first wheel is in said first operational position and said second wheel is in said second operational position;

(h) an upper chassis operatively and movably secured to said lower chassis;

(i) a rotatable, omnidirectional, third wheel operatively secured to said upper chassis, said third wheel permitting movement of said lower chassis and of said upper chassis in any direction generally parallel to or horizontal with the floor; and (j) means for mechanically or electrically moving said upper chassis in a selective and controlled manner along a predetermined third path relative to said lower chassis between a retracted position and an extended position.

2. The apparatus of claim 1, further comprising a protective shield secured to said lower chassis to shield said lower chassis from drawing in contaminants or debris.

3. The apparatus of claim 2, further comprising at least one wiper blade or washer secured to said lower chassis about said first wheel and about said second wheel to shield said lower chassis from drawing in contaminants or debris.

4. The apparatus of claim 1, wherein said first wheel and said second wheel are drive wheels capable of moving said lower chassis in a precise and predictable manner.

5. The apparatus of claim 1, further comprising:

(a) means for coupling said first wheel to said lower chassis, said first coupling means enabling said first wheel to rotate about said first generally horizontal axis and to rotate about said first vertical axis; and (b) means for coupling said second wheel to said lower chassis, said second coupling means enabling said second wheel to rotate about said second generally horizontal axis and to rotate about said second vertical axis.

6. The apparatus of claim 5, wherein said means for selectively rotating said first wheel about said first vertical axis between said first traveling position and said first operational position further comprises:
(a) a first pulley operatively secured to said means for coupling said first wheel to said lower chassis;
(b) a mechanically or electrically powered first rotator motor operatively secured to said lower chassis;
(c) a second pulley operatively secured to said first rotator motor; and
(d) a first drive belt operatively secured to and positioned between said first pulley and said second pulley.

7. The apparatus of claim 6, wherein said means for selectively rotating said second wheel about said second vertical axis between said second traveling position and said second operational position further comprises:
(a) a third pulley operatively secured to said means for coupling said second wheel to said lower chassis; and
(b) a second drive belt operatively secured to and positioned between said third pulley and said second pulley.

8. The apparatus of claim 6, wherein said means for selectively rotating said second wheel about said second vertical axis between said second traveling position and said second operational position further comprises:
(a) a third pulley operatively secured to said means for coupling said second wheel to said lower chassis;
(b) a mechanically or electrically powered second rotator motor operatively secured to said lower chassis;
(c) a fourth pulley operatively secured to said second rotator motor; and
(d) a second drive belt operatively secured to and positioned between said third pulley and said fourth pulley.

9. The apparatus of claim 1, wherein said means for mechanically or electrically rotating said first wheel in a selectively controlled manner further comprises a first drive motor operatively secured to said lower chassis.

10. The apparatus of claim 9, wherein said means for mechanically or electrically rotating said second wheel in a selectively controlled manner comprises a second drive motor operatively secured to said lower chassis.

11. The apparatus of claim 1, wherein said means for mechanically or electrically rotating said second wheel in a selectively controlled manner further comprises a second drive motor operatively secured to said lower chassis.

12. The apparatus of claim 1, wherein said lower chassis further comprises one or more tracks into which at least a portion of said upper chassis is operatively and movably secured.

13. The apparatus of claim 1, wherein said third wheel moves with said upper chassis between said retracted position and said extended position to provide support and stability to said upper chassis.

14. The apparatus of claim 1, wherein said means for mechanically or electrically moving said upper chassis in a selective and controlled manner along said predetermined third path relative to said lower chassis between said retracted position and said extended position comprises:
(a) a worm-screw operatively secured to said upper chassis;
(b) a drive nut operatively secured to said lower chassis and operatively engaged with said worm-screw; and
(c) a scanner motor operatively connected to said worm-screw to selectively rotate said worm-screw in a predetermined and controlled manner.

15. The apparatus of claim 1, wherein said means for mechanically or electrically moving said upper chassis in a selective and controlled manner along said predetermined third path relative to said lower chassis between said retracted position and said extended position comprises:
(a) a worm-screw operatively secured to said lower chassis;
(b) a drive nut operatively secured to said upper chassis and operatively engaged with said worm-screw; and
(c) a scanner motor operatively connected to said worm-screw to selectively rotate said worm-screw in a predetermined and controlled manner.

16. The apparatus of claim 1, further comprising a cabinet operatively secured to said upper chassis.

17. The apparatus of claim 16, further comprising a handle secured to said cabinet.

18. The apparatus of claim 16, wherein said upper chassis supports and further comprises means for conducting a medical scan of a portion of the body of the patient.

19. The apparatus of claim 18, wherein said means for conducting a medical scan of a portion of the body of the patient comprises a mobile: x-ray-imaging system, a C-arm x-ray-imaging system, an angiographic-imaging system, a cardiac-imaging system, a thermal-imaging system, an ultrasonic-imaging system, or a magnetic-resonance-imaging system.

20. The apparatus of claim 1, further comprising a hand-held control unit to activate or deactivate said remotely actuated means for selectively rotating said first wheel about said first vertical axis, said remotely actuated means for selectively rotating said second wheel about said second vertical axis, said remotely actuated means for mechanically or electrically rotating said first wheel about said first horizontal axis, or said remotely actuated means for mechanically or electrically rotating said second wheel about said second horizontal axis.

21. The apparatus of claim 20, wherein said hand-held control unit is remote controlled.

22. The apparatus of claim 21, wherein said hand-held control unit is radio controlled or infrared controlled.

* * * * *